(12) United States Patent
Benyacoub et al.

(10) Patent No.: US 10,064,426 B2
(45) Date of Patent: *Sep. 4, 2018

(54) PROBIOTICS FOR USE IN EXPECTING FEMALE MAMMALS FOR ENHANCING THE IMMUNITY OF THEIR OFFSPRING

(71) Applicant: NESTEC S.A., Vevey (CH)

(72) Inventors: Jalil Benyacoub, Lausanne (CH);
Stephanie Blum-Sperisen, Pully (CH);
Florence Rochat, Montreux (CH);
Thierry Von der Weid, St. Legier (CH)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/230,865

(22) Filed: Aug. 8, 2016

(65) Prior Publication Data
US 2017/0006908 A1    Jan. 12, 2017

Related U.S. Application Data

(62) Division of application No. 12/935,149, filed as application No. PCT/EP2009/052869 on Mar. 11, 2009, now Pat. No. 9,414,621.

(30) Foreign Application Priority Data

Mar. 28, 2008 (EP) ...................... 08153566

(51) Int. Cl.
| | | |
|---|---|---|
| A23L 33/135 | (2016.01) | |
| A23L 33/21 | (2016.01) | |
| A61K 9/00 | (2006.01) | |
| A61K 35/741 | (2015.01) | |
| A61K 35/745 | (2015.01) | |
| A61K 35/747 | (2015.01) | |
| A61K 39/09 | (2006.01) | |
| A61K 35/00 | (2006.01) | |

(52) U.S. Cl.
CPC ............ *A23L 33/135* (2016.08); *A23L 33/21* (2016.08); *A61K 9/0053* (2013.01); *A61K 35/741* (2013.01); *A61K 35/745* (2013.01); *A61K 35/747* (2013.01); *A61K 39/09* (2013.01); *A23V 2002/00* (2013.01); *A23V 2200/30* (2013.01); *A23Y 2220/73* (2013.01); *A61K 2035/115* (2013.01)

(58) Field of Classification Search
None
See application file for complete search history.

(56) References Cited

U.S. PATENT DOCUMENTS

| | | |
|---|---|---|
| 7,862,808 B2 | 1/2011 | Isolauri et al. |
| 2001/0036453 A1 | 11/2001 | Reid et al. |
| 2003/0017192 A1 | 1/2003 | Kanafani et al. |
| 2004/0110270 A1 | 6/2004 | Dennin |
| 2006/0013806 A1 | 1/2006 | Isolauri et al. |
| 2006/0165669 A1 | 7/2006 | Reid et al. |
| 2006/0171936 A1 | 8/2006 | Gueniche et al. |

FOREIGN PATENT DOCUMENTS

| | | |
|---|---|---|
| WO | 0197822 | 12/2001 |
| WO | 2006007526 | 12/2001 |
| WO | 0207533 | 1/2002 |
| WO | 2004112507 | 12/2004 |
| WO | WO 2006/108824 | * 10/2006 |
| WO | 2007039313 | 4/2007 |
| WO | 2007/105945 | 9/2007 |
| WO | 2007/144334 | 12/2007 |
| WO | WO 2008/116700 | * 2/2008 |

OTHER PUBLICATIONS

Bliss, Roasalie, "Boosting Immunity Using Beneficial Bacteria" Agricultureal Res. Mag., vol. 54. Nov. 2006.
Kalliomaki, Marko et al., "Probiotics and prevention of atopic disease: 4-year follow-up of a randomised placebo-controlled trial" The Lancet, vol. 361, Mar. 31, 2003.
Schultz, Michael et al., "Administrative of oral Probiotic Bacteria to Pregnant Women Causes Temporary Infantile Colonization" J Pediatr Gastroenterol Nutr., vol. 38, Mar. 2004.
Agricultural Res. Mag. vol. 54, No. 11, 2006. Table of Contents. Two pages.
US Department of Agriculture, "Beneficial Bacteria Boost Intestinal Health" Host: http://wwww.ars.usda.gov/is/or/2006/061117.htm Nov. 26, 2007.
Archive, "Beneficial Bacteria Boost Intestinal Health" Host: https://web.archive.org/web/20071126095332/http://www.ars.usda.gov/ Nov. 26, 2007, Oct. 21, 2015.
Bliss, Rosalie, "Boosting Immunity Using Beneficial Bacteria" International Pest Control, vol. 49, Mar. 2007.
Reid, Gregor et al., "Taking probiotics during pregnancy Are they useful therapy for mothers and newborns?" Canadian Family Physician, vol. 51, Nov. 2005.
Kaplas, Niina et al., "Dietary Counseling and Probiotic Supplementation During Pregnancy Modify Placental Phospholipid Fatty Acids" Lipids, vol. 42, Jul. 24, 2007.
Fukushima, Yoichi et al., "Effect of Probiotic Formula on Intestinal Immunoglobulin A Production in Healthy Children" Int. J. Food Microbiol., vol. 42, Jun. 30, 1998.
Rautava, Samuli et al., "Probiotics during pregancy and breast-feeding might confer immunomodulatory protection against atopic disease in the infant", J. Allergy Clin. Immunol., vol. 109, Jan. 2002.
Communication of a notice of opposition for Application No./Patent No. 13160279.9-1456 / 2612562 dated Nov. 2, 2015.

(Continued)

*Primary Examiner* — Oluwatosin A Ogunbiyi
(74) *Attorney, Agent, or Firm* — K&L Gates LLP

(57) ABSTRACT

The present invention relates to the use of probiotic on expecting female mammals to boost the immune status of an offspring. The use can induce an enhanced response of the offspring after birth to an infectious antigenic exposure. Ultimately the use of probiotic in expecting females can induce a better protection of their offspring against infectious diseases.

18 Claims, 4 Drawing Sheets

(56) References Cited

OTHER PUBLICATIONS

Extended European Search Report for European Patent Application No. EP13179351 dated Oct. 17, 2013.
International Search Report for International Patent Application No. PCT/EP2009/052869 dated May 5, 2009.
M. Rinne, et al., "Probiotic Intervention in the First Months of Life: Short-Term Effects of Gastrointestinal Symptoms and Long-Term Effects on Gut Microbiota," Journal of Pediatric Gastroenterology and Nutrition, vol. 43, No. 2, Aug. 2006, pp. 200-205, XP0091 03941.
K. Laitenen et al., "Evaluation of diet and growth in children with and without atopic eczema: follow-up study from birth to 4 years," British Journal of Nutrition, vol. 94, 2005, pp. 565-574, XP002490047.

* cited by examiner

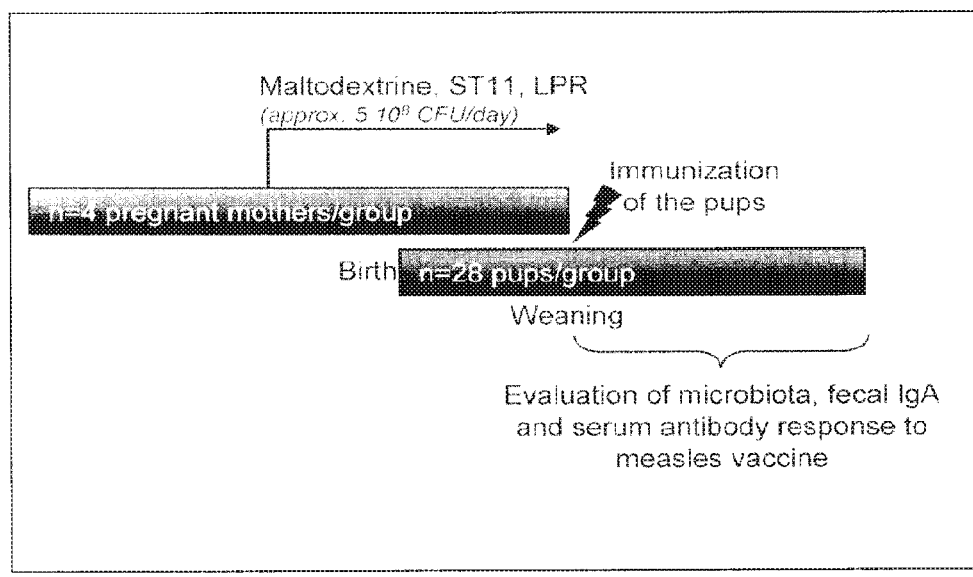
Fig. 1: Experimental procedure (study 1)

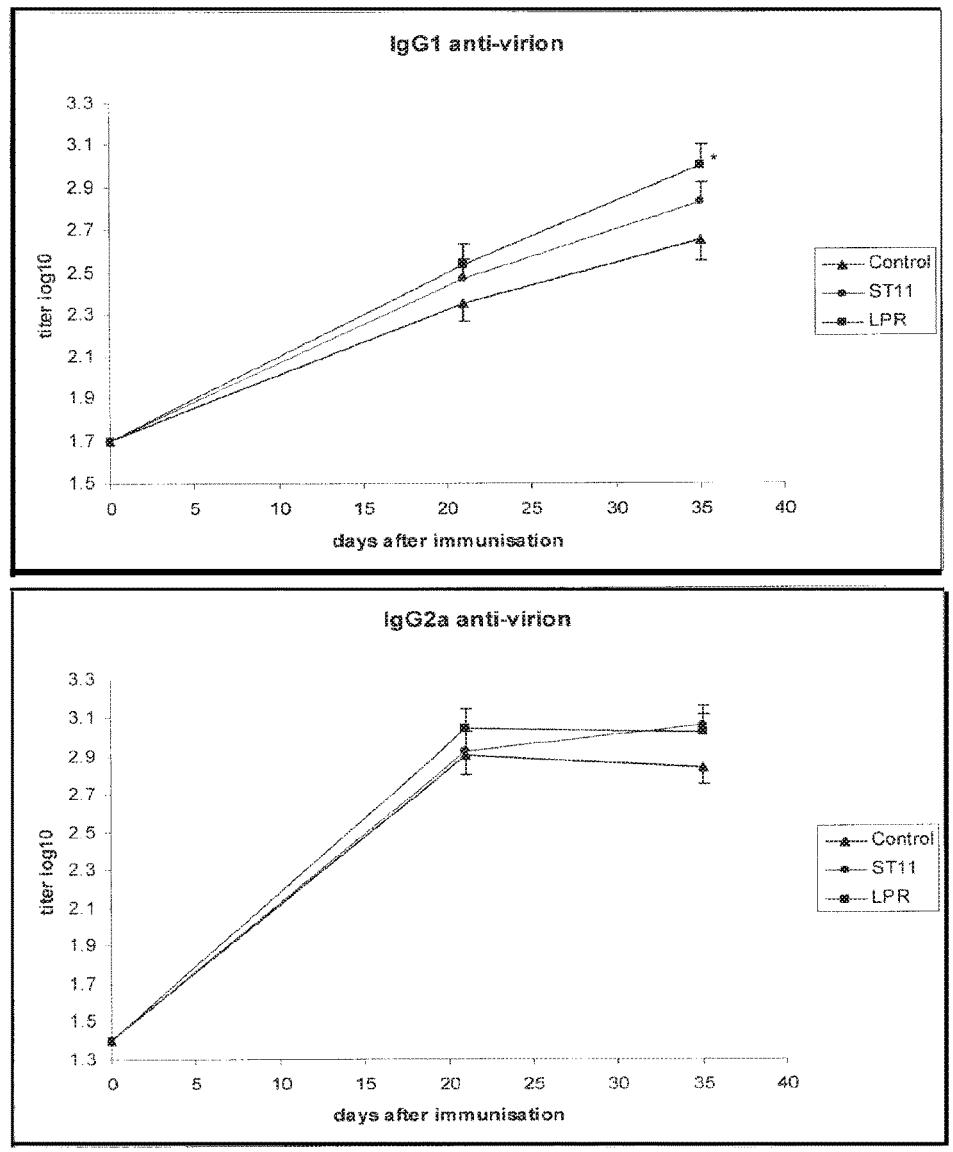
Fig 2 : Specific-measles antibody responses. Means values ± SEM. *: $P=0.03$ compared to control.

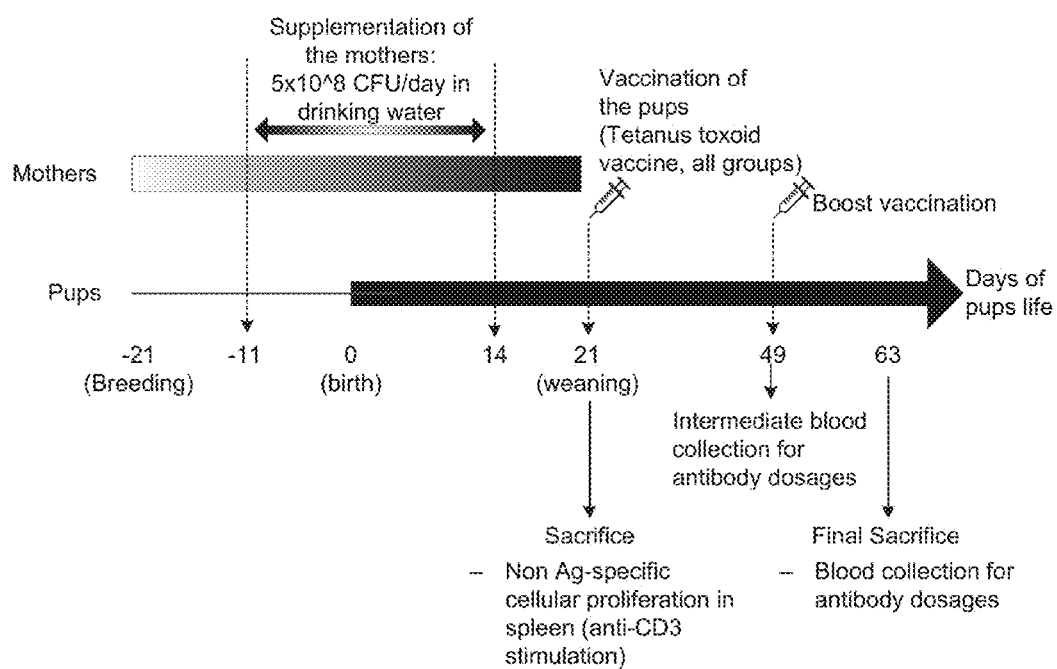
Fig.3: Experimental design (study 2)

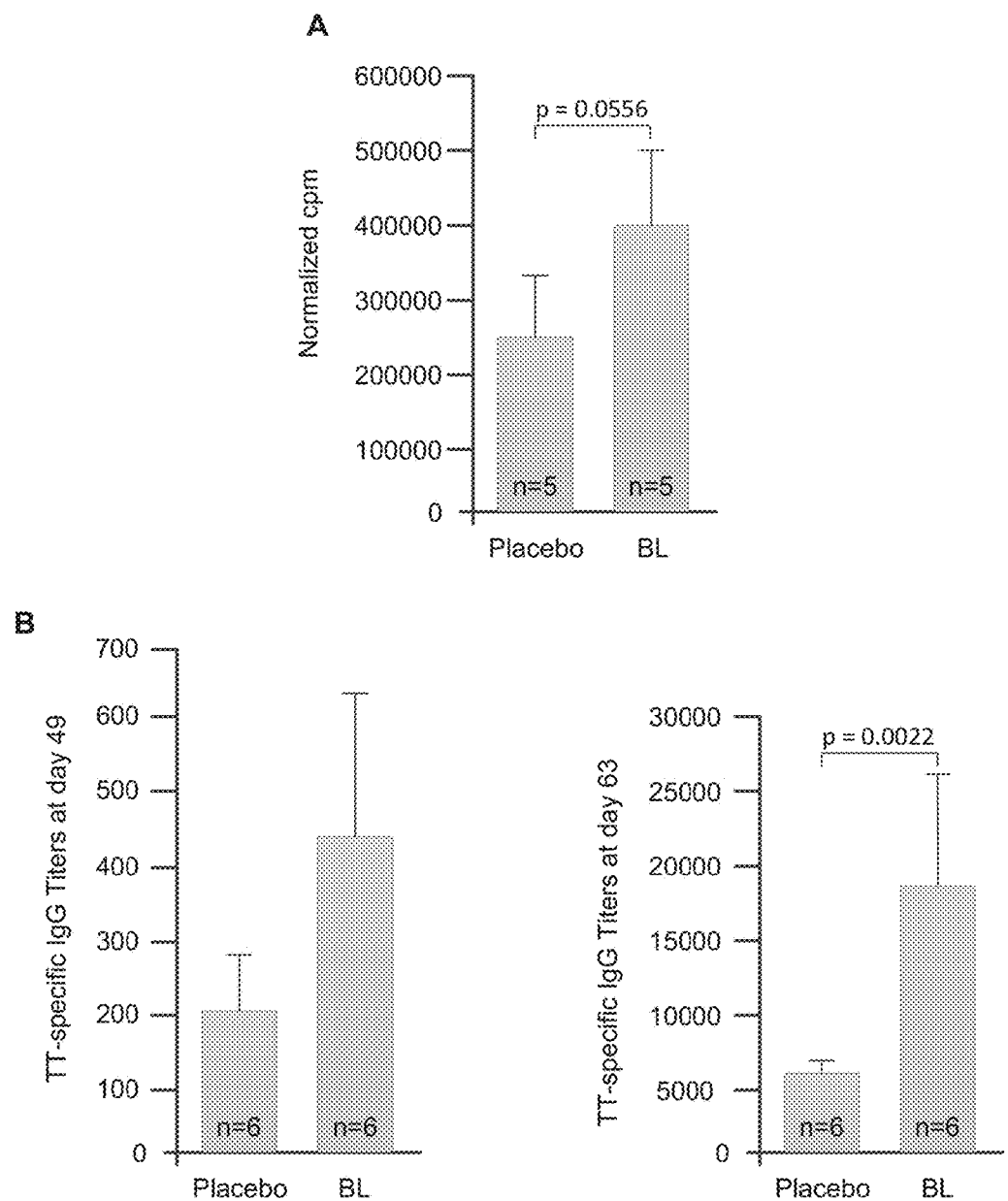
Fig. 4: System immune responses of (A) non-antigen specific spleen T cell and (B) anti-TT IgG antibody

PROBIOTICS FOR USE IN EXPECTING FEMALE MAMMALS FOR ENHANCING THE IMMUNITY OF THEIR OFFSPRING

PRIORITY CLAIM

The present application is a divisional application of U.S. patent application Ser. No. 12/935,149, filed on Sep. 28, 2010, which is a National Stage of International Application No. PCT/EP09/52869, filed on Mar. 11, 2009, which claims priority to European Patent Application No. 08153566.8, filed Mar. 28, 2008, the entire contents of each of which are being incorporated herein by reference.

FIELD OF THE INVENTION

This invention relates to the use of probiotics bacteria in the manufacture of a nutritional composition for expecting female mammals to enhance the immunological status in their newborn offspring.

BACKGROUND

The immunological status of newborn is an important issue. This status encompasses to the protection present at the birth of the infant and to the acquisition of such immunological protection during the first hours, days or weeks of the infant life. The ability to acquire and maintain such protection is a crucial factor in the health of the infant faced with his new environment. In humans these issues are of the highest importance for the health of the population.

Maintaining the expecting mothers in good health condition during gestation is a key factor for promoting the health of the offspring during gestation and after birth. General health factors that are known include their nutritional habits, their micro-nutriment intake, their infectious history and also relate to their immunological status. For example deficiencies in some minerals, vitamins or substances (such as folic acid) can affect the development of the fetus and also affect post-natal infant development. The nutrition of the mother plays in that respect a key role in the future health of the infants and much efforts have been made to monitor and improve the nutritional balance of the expecting mothers. Food supplements or simply general eating guidelines are essential in that respect.

Along with general nutritional guidance for expecting mothers, it is now recognized that some specific food can promote the proliferation of a specific microbiota in the gastro-intestinal tract of the expecting mother. The balanced microbiota in turn may have an effect on the host.

The use of prebiotics, i.e. nutritional substances for improving the intestinal microbiota of a host, has been described for example in WO 02/07533 for its health benefits in females.

Moreover, it has been claimed in WO2007/105945A that feeding of the expecting mothers with prebiotics ingredients, especially certain type of non digestible saccharides could improve the microbiota and/or the immune system of the offspring.

Complementing the nutritional intake with micro-organisms, preferably live micro-organisms, has also been demonstrated to improve the microbiota balance of the intestinal tract of the host. The modulation of the microbiota of the intestinal tract by specific live micro-organisms has been shown to bring particular positive physiological effects. For example the immune response induced by specific types of probiotic bacteria has been widely studied and described ("Cross talk between probiotics bacteria and the host immune system", The journal of nutrition. Blaise Corthesy et al., supplement, 2007, pages 781S-790S). As described in the scientific literature, specific strains of micro-organisms have been shown more particularly to have beneficial effects. *Bifidobacterium, Lactobacillus acidophilus*, and *Lactobacillus caseii* are generally known examples of families shown to have probiotics effects.

It is hypothesized that probiotics, as other commensals, will influence immune functions of the host either via modulation of the microbiota composition and/or metabolic activity or through a direct interaction with the immune system underlying the gut mucosa. Following this interaction, immune functions will be activated as reflected by the release of immune mediators (cytokines), production of antibodies and activation of lymphocytes as well as other immune cells. These activated cells, cytokines and/or bacterial compounds will exert immune modulatory functions at different location of the body through the blood circulation. In that respect, it is postulated that a beneficial effect on the immune status of the mother through probiotic supplementation may already influence fetal immune development. Moreover, it is also known that immune cells and other bioactive factors originating from the gut of the mother could be transported to the breast milk via an entero-mammary transport pathway and transmitted to the neonate during lactation. Therefore, it is worth to further hypothesize that supplementation of pregnant mothers might promote an enrichment of the breast milk with immune factors that would contribute to support neonatal immune development.

Securing the healthy future of offspring is a well recognized need. More specifically insuring the best development and maturation of the immune system of the offspring is of the highest importance.

Conventionally, beside medical treatments responding to specific medical conditions, emphasis is put on a good nutritional balance of the expecting mothers. Not much is however known on how to specifically enhance the immune status of the offspring during the gestation period.

There is however a need for a further step in securing the healthy future of the offspring, using the most recent finding on nutrition.

There is therefore a need for positively impacting the health of the offspring by a targeted nutritional diet of the expecting mothers.

There is in particular a need to help guaranteeing the best immune system in the offspring, in order to best prepare them to the early life antigenic challenges as well as to enhance the future maturation of their immune system to better promote protection during later infancy.

There is a need to impact the building of the immune system of the offspring at the earliest possible stage during and all along the gestation as well as the early phases of their new born life when the immune system is maturing at high pace.

There is a need to boost the ability of the immune system of the offspring to react against antigens in general and against infectious diseases in particular.

There is a need to deliver these benefits by means that are both efficient and deprived of negative impact on the expecting mothers and or their offspring.

SUMMARY

In a first aspect, the present invention provides the use of probiotics on expecting female mammals in the manufacturing of a composition for boosting the immunity of their offspring after birth.

In a second aspect, the present invention provides the use of specific probiotics organisms such as *Bifidobacterium, Lactobacillus, Streptococcus, Enterococcus* and *Saccharomyces*, in expecting female humans for boosting the immunity of their offspring after birth.

In a third aspect, the present invention provides the use of the probiotics during the gestation period and/or during the lactation period of the offspring.

In another aspect of the invention the probiotics are administered in or with the food or drinks of the expecting mother, and together with other active ingredients such as prebiotics or other dietary supplements.

The invention further extends to the composition used by the above methods for the purposed cited.

BRIEF DESCRIPTION OF THE DRAWINGS

FIGS. 1 and 3 highlight schematically the experimental procedures of the studies 1 and 2 respectively described.

FIGS. 2 and 4 show the results of the studies indicating an immune boost in the offspring. In FIG. 4, A shows the systemic immune responses of non-antigen specific spleen T cell at 3 weeks of proliferation, and B shows the anti-TT lgG antibody responses at 4 weeks after the first immunization (left panel) and 2 weeks after the boost (right panel).

DETAILED DESCRIPTION

Definitions:

In this specification, the following terms have the following meanings:

"Expecting female mammals" are female mammals that have at least one fecunded ovocyte in development in their uterus. Preferentially, female humans (i.e. mothers or mothers-to-be) are considered by this invention.

"Probiotic" means microbial cell preparations or components of microbial cells with a beneficial effect on the health or well-being of the host, (Salminen S, Ouwehand A. Benno Y. et al "Probiotics: how should they be defined" Trends Food Sci. Technol. 1999:10 107-10). The probiotic can comprise a unique strain of micro-organism, of a mix of various strains and/or a mix of various micro-organisms. In case of mixtures the singular term "probiotic" can still be used to designate the probiotic mixture or preparation.

"Prebiotic" generally means a non digestible food ingredient that beneficially affects the host by selectively stimulating the growth and/or activity of micro-organisms present in the gut of the host, and thus attempt to improve host health.

"Offspring" relates to the newly-born or to-be-born infant from the subject female mammals. In particular, it includes the progeny still in gestation. Preferentially the juvenile phase/infancy phase is considered by the present invention (i.e. up to adolescence in humans—12-14 years), more preferentially the present invention relates to the immune status of the offspring in the early infancy (up to 2 to 4 years of age in humans).

The inventors have found that the administration of probiotics to expecting female mammals can impact the immune system of the offspring, and more particularly can boost the immune system of the offspring such as to enable a better and stronger response of the immune system after exposure to antigens. The modulation of immune system of the offspring can happen very early in their intrauterine life or early phase of extra uterine life, when their immune system is maturing.

The inventors have evidenced the boosting effect in absence of obvious direct contact between the intestinal system of the offspring and the probiotics composition administered to the expecting females, i.e. during the intrauterine life of the offspring.

Further the inventors have found that such composition comprising probiotics can also have a beneficial effect on the immune system of the offspring during the lactation period.

Without being bound by the theory, it is speculated that the partial colonization of the intestinal tract of the expecting females by the probiotic induces the creation of a molecular signal. It is believe that the offspring receives and reacts to this molecular signal. It is further believed that the immune system of the offspring is affected by that signal. That signal has a positive effect on the maturation of the immune system of the offspring. This can lead to a better ability to respond to antigens after birth. It is further speculated that the signal can be transmitted to the offspring during the lactation period, more specifically if there was a preconditioning to the signal during the gestation period of the offspring.

Expecting Females.

The use of and the composition of the present invention is performed on and administered to expecting females mammals, i.e. females which are due to give birth to offspring. The use considered by the present invention extends from the conception of the offspring (fecundation) through the full gestation period up to the delivery of the offspring. It can also extend to the lactation period up to the weaning. Partial weaning, up to the full termination of the lactation, is also included in the present invention. It is not excluded that the use considered by the invention also extends to the period immediately preceding the fecundation that has an impact on the health status of the females, and indirectly on the health status of the offspring.

The mammals can be pregnant humans females. In such case the gestation period is about 9 months and the lactation period can considerably vary according to habits, culture and health status of the females. The female mammals can also be other female mammals including horses and pets such as cats and dogs. Other expecting female mammals are not excluded from this invention.

Probiotic Micro-Organisms.

The probiotic micro-organisms considered by this invention can include any probiotic selected form the group comprising of *Bifidobacterium, Lactobacillus, Streptococcus, Enterococcus* and *Saccharomyces* or mixtures thereof, preferably selected from the group consisting of *Bifidobacterium longum, Bifidobacierium lactis, Lactobacillus acidophilus, Lactobacillus rhamnosus, Lactobacillus paracasei, Lactobacillus johnsonii, Lactobacillus plantarum, Lactobacillus salivarius, Lactobacillus reuteri, Enterococcus faecium, Streptococcus* sp. and *Saccharomyces boulardii* or mixtures thereof. Other probiotic micro-organisms are not excluded from this invention provided they are able to deliver the immune boost effect described.

More preferably the probiotic is selected from the group comprising of *Lactobacillus rhamnosus* CGMCC 1.3724 (nick name NCC4007 and LPR), *Bifidobacterium lactis* CNCM 1-3446 sold inter alia by the Christian Hansen company of Denmark under the trade mark Bb12 (nick mane NCC2818), *Bifidobacterium longum* ATCC BAA-999 sold by Morinaga Milk Industry Co. Ltd. of Japan under the trade mark BB536. *Lactobacillus johnsonii* CNCM 1-1225 (nick name NCC533 and La1), *Lactobacillus fermentum* VRI 003 sold by Probiomics (Australia), under the trademark PCC, *Bifidobacterium longum* CNCM 1-2170, *Bifidobacterium longum* CNCM 1-2618, *Bifidobacterium breve* sold by Danisco (Denmark) under the trade mark Bb-03, *Bifidobacterium breve* sold by Morinaga (Japan) under the trade mark M-16V and the strain of *Bifidobacterium breve* sold by Institut Rosell (Lallemand) (Canada) under the trade mark R0070. *Lactobacillus paracasei* CNCM 1-1292. *Lactobacillus rhamnosus* ATCC 53103 obtainable inter alia from Valio Oy of Finland under the trade mark LGG, *Enterococcus faecium* SF 68, and mixtures thereof. A preferred probiotic is *Lactobacillus rhamnosus* CGMCC 1.3724.

Doses of Probiotic.

The probiotic can be present in the composition in a wide range of % provided that the specific probiotic used deliver the immunity boosting effect described. However, preferably, the probiotic is present in the composition in an amount equivalent to between $10^3$ and $10^{10}$ cfu/g of dry composition (cfu=colony forming unit). This expression includes the possibilities that the bacteria are live, inactivated or dead or even present as fragments such as DNA or cell wall materials. In other words, the quantity of bacteria which the formula contains is expressed in terms of the colony forming ability of that quantity of bacteria as if all the bacteria were live irrespective of whether they are, in fact, live, inactivated or dead, fragmented or a mixture of any or all of these states. Preferably the probiotic is present in an amount equivalent to between $10^4$ to $10^9$ cfu/g of dry composition, even more preferably in an amount equivalent to between $10^6$ and $10^8$ cfu/g of dry composition.

Method of Administration.

The composition can be administered to the expecting females by a various ways as long as it induces a contact between the composition and the gastro-intestinal tract of the females. Preferably the composition is administered as part of the food, drinks or dietary supplements of the females. The composition can also be administered in a pharmaceutical composition. Preferably the administration is oral or enteral. Oral administration is most preferred as it has a less traumatic impact on the females. However in pathological conditions or when enteral feeding is otherwise used, the administration of the composition can be added to the enteral feeding.

Administration with Other Compounds.

In any case, the composition can be administered alone (pure or diluted in water for example) or in a mixture with other compounds (such as dietary supplements, nutritional supplements, medicines, carriers, flavors, digestible or non-digestible ingredients). Vitamins and minerals are examples of typical dietary supplements. In a preferred embodiment the composition is administered together with other compounds that enhance the described effect on the immunity of the offspring. Such synergistic compounds can be a carrier or a matrix that facilitates the delivery of the probiotics to the intestinal tract of the female, preferably in an active form. Such synergistic compounds can also affect the health status or metabolism of the expecting female such as to enhance the effect of the composition on the immune system of the offspring. Such synergistic compounds can be other active compounds that synergistically or separately influence the immune response of the infant and/or potentialize the effect of the probiotic. Example of such synergistic compounds is maltodextrine. One of the effects of maltodextrin is to provide a carrier for the probiotic, enhancing its effect, and to prevent aggregation. Other examples include known prebiotic compounds such as carbohydrate compounds selected from the group consisting of inulin, fructooligosaccharide (FOS), short-chain fructooligosaccharide (short chain FOS), galacto-oligosaccharide (GOS), xylooligosaccharide (XOS), glanglioside, partially hydrolysed guar gum (PHGG) acacia gum, soybean-gum, Lactowolfberry, wolfberry extracts or mixture thereof. Other carbohydrates can be present such as a second carbohydrate acting in synergy with the first carbohydrate and that is selected from the group consisting of xylooligosaccharide (XOS), gum, acacia gum, starch, partially hydrolysed guar gum or mixture thereof.

The carbohydrate or carbohydrates can be present at about 1 g to 20 g or 1% to 80% or 20% to 60% in the daily doses of the composition. Alternatively the carbohydrates are present at 10% to 80% of the dry composition. In any case however the daily dose of carbohydrate should comply with the published safety guidelines and regulatory requirements. For children, a typical limit, for example, is a maximum of 6 g/L/day.

In an embodiment, a nutritional composition preferably comprises a source of protein. Dietary protein is preferred as a source of protein. The dietary protein may be any suitable dietary protein; for example animal protein (such as milk protein, meat protein or egg protein); vegetable protein (such as soy protein, wheat protein, rice protein, and pea protein); a mixture of free amino acids; or a combination thereof. Milk proteins such as casein, whey proteins and soy proteins are particularly preferred.

The composition may also comprise a source of carbohydrates and/or a source of fat.

If the composition of the invention is a nutritional composition and includes a fat source, the fat source preferably provides about 5% to about 55% of the energy of the nutritional composition; for example about 20% to about 50% of the energy. Lipid making up the fat source may be any suitable fat or fat mixture. Vegetable fat is particularly suitable; for example soy oil, palm oil, coconut oil, safflower oil, sunflower oil, corn oil, canola oil, lecithin, and the like. Animal fat such as milk fat may also be added if desired.

An additional source of carbohydrate may be added to the nutritional composition. It preferably provides about 40% to about 80% of the energy of the nutritional composition. Any suitable carbohydrate may be used, for example sucrose, lactose, glucose, fructose, corn syrup solids, maltodextrin or a mixture thereof.

Additional dietary fiber may also be added if desired. If added, it preferably comprises up to about 5% of the energy of the nutritional composition. The dietary fiber may be from any suitable origin, including for example soy, pea, oat, pectin, guar gum, acacia gum, fructooligosaccharide or a mixture thereof.

Suitable vitamins and minerals may be included in the nutritional composition in an amount to meet the appropriate guidelines.

One or more food grade emulsifiers may be included in the nutritional composition if desired; for example diacetyl tartaric acid esters of mono- and di-glycerides, lecithin and mono- or di-glycerides or a mixture thereof. Similarly suitable salts and/or stabilizers may be included. Flavors can be added to the composition.

Administration Period.

The administration period starts with the fecundation or as soon as possible after fecundation (resp. after the mother-to-be is made aware of her pregnancy). However the administration period can also start earlier. For example, the administration period can precede the fecundation by 1 or 2 months. In such case, it is believed that the health status of the mother-to-be fecunded has an impact of the health status of the offspring-to-be. The administration period can also start relatively late in the pregnancy, preferably at month 3, 5 or 7 of the pregnancy (when considering human females)

or in corresponding periods for other mammals. A very late start of the administration of the composition can also be considered, i.e. at or around month 8 or 9 (a few weeks before birth). In such case, it is speculated that the effect on the immune system of the offspring is a short term and rapid effect, best preparing it for the exposure to antigens after birth. The period of administration can be continuous (for example up and including lactation up to weaning), or discontinuous. Preferably the period of administration is continuous for better prolonged effect. However it is speculated that a discontinuous pattern (for example daily administration during 1 week per month) can provide "discontinuous immune boost signals" that induce positive effects on the offspring. The duration of the administration may vary. If positive effects are expected with relatively short duration of administration (for example daily administration during 1 week or 1 month), long durations are believed to provide enhanced effect (for example duration of 3, 5, or 8 months in humans, and corresponding periods in other mammals). Preferably the administration period covers substantially the full length of the gestation period. In one embodiment it covers more than 50%, more than 70%, or more than 80% of the gestation period. The duration of administration can also cover all or a part of the lactation period.

Most preferably it also covers the full length of the lactation period. The duration can cover 0%, 30% or more, 50% or more or 80% or more of the lactation period. In one particular embodiment the period of administration of the composition can cover the lactation period (all or part of it) but not the gestation period; in that case the benefits of the composition are transmitted through the female milk to the offspring. Most preferably the administration period covers a part (or all) of the gestation period and part (or all) of the lactation period. Preferably the administration is be done in daily intake (to be taken once or twice a day), or weekly intake (to be taken one or twice a week).

In one embodiment, the composition is also administered directly to the offspring provided that the mother has received the composition during gestation. Preferably the composition is administered, most preferably orally, directly to the offspring during lactation or after partial or full weaning. The dual exposure of the mother (during gestation) and of the offspring (direct administration) to the composition can indeed provide enhanced benefits in a synergistic way. It is speculated that the exposure during gestation induces a preconditioning of the offspring to better respond to the later direct administration.

Effect of the Composition.

The composition of the invention administered to expecting female mammals induces the boost of the immunity of the offspring. That boost is particularly measurable after birth but may start during the gestation period.

Specifically, the term "boosting immunity" used therein excludes the allergic responses. The term "boosting immunity" is defined as boosting the innate immune functions and promoting specific immune response to antigens. The innate immune response can be cellular responses, phagocytic activity, leucocytic activity and/or polyreactive antibodies. The specific immune response can be cell activation and/or specific antibody responses. The term "boosting immunity" can comprise or can be defined as the enhancement of immune defenses of the body and/or the enhancement of the capability of the body to respond to infectious antigenic challenges. The antigenic challenges can be viral and/or bacterial and/or parasitic agents or their antigen derivatives, sub-units, cell-surface compounds and/or toxins.

In one embodiment, the composition of the invention reinforces the transmission of immune competences from the females to the offspring. Doing so, the composition is able to provide the offspring with better chances to endure the challenges of their early life. Ultimately the composition helps the offspring to have a best start in life and/or to better protected against infections.

In one embodiment such boosting effect is an increase in the ability of the offspring to respond to an antigenic exposure. At birth the immune system of the infant is both in a state that enables him to respond appropriately to antigenic exposures and in a state of rapid maturation. The exposure to antigens also participates to enhance the maturation of the immune system. After birth all infants are naturally exposed to environmental or pathogenic antigens. The immune system of the offspring responds to such exposure. In one embodiment of the present invention the immune system of the offspring is able to respond in a more efficient way to exposure to antigens. In one embodiment the response to the antigenic exposure can be measured by the dosage of antibodies specific to the antigen. In the context of the invention a quantitative as well as qualitative elevation of the specific antibodies can be measured. In one embodiment such elevation can be measured in the serum and/or in the saliva and/or in the feces of the offspring exposed to the antigens. In one embodiment the response to the antigenic exposure comprises an elevation of the total poly-reactive antibodies, preferably in the serum and/or in the saliva and/or the feces of the offspring. In one embodiment the response to the antigenic exposure comprises an elevation of the cellular immune response in the blood of the offspring, preferably an increase in number and/or increase in activity of the leucocytes of the offspring (for illustration, see results of example 2). It is understood that the type of response is highly dependent on the type of exposure, although some antigens can induce a complex immune response measurable by more than one of the above cited effects (for example elevation of specific antibodies and elevation of polyreactive antibodies, and/or elevation of cellular immune response). The measurements of the immune response can be done by conventionally known immuno-assay methods, such as cellular counts, antibodies-assays, phagocytic activity as well as cytotoxic cell activity (neutrophils and natural killer cells activity) dosage of immunity markers, including cytokines, growth factors as well as cell-surface immune markers and the like. The elevation is measured against the levels in the corresponding samples from offspring which mothers were not exposed to the composition of the invention (=control samples).

An antigenic exposure that is of particular relevance in the context of the invention includes but is not limited to exposure to viruses preferably rotaviruses and adenoviruses, or exposure to infective bacteria, preferably *Escherichia coli*, *Vibrio cholerae*, salmonellae, clostridia, shigella, or exposure to infective parasites infection, preferably *Giardia lamblia*, *Entamoeha histolytica* and *Cryptosporidium* spp or mixtures thereof. It is of particular interest for the health status of the infants to exhibit a better ability to respond to such pathogenic exposure. This can participate to a better protection of the offspring against these pathogens, and ultimately to better protect them against the corresponding infections induced by these pathogens. More generally it can participate to a better protection of the offspring against many types of pathogens (=enhanced immune system in general). Positive effect on allergies can also be contemplated within the scope of this invention, as the effect on the immune system can be a better balanced and better controlled response to allergens.

The boosting effect on the immune system of the offspring can reach a maximum during the lactation period, or during juvenile phase/childhood. For humans the maximum of the boost is preferably achieved between birth (day 0) and months 24 of life, more preferably between birth (day 0) and day 180 of life. In is not excluded that the boosting effect can last until the young adulthood phase of the life of the offspring. For non-human mammals corresponding periods have to be considered.

The invention will now be further illustrated by reference to the following example:

Example 1

Mice Study 1
Material and Methods:
Conventional six-week-old female BALB/c mice (18-20 g) were used in all experiments, purchased from Charles River (Domaine des Oncins, BP 010969592. L'Arbresle Cedex, France). The mice were housed under specific pathogen free conditions at the Clinique Medical Universitaire of Geneva (CMU-Geneva) animal facility, and 6 to 8 infant mice from each litter were allotted to each study group.

Animals had free access to regular conventional diet. Pregnant mice received probiotic or placebo powders suspended in the drinking water. The drinking water was changed every day. Three groups were compared:
Group A control (Maltodextrine)
Group B *Lactobacillus paracsei* CNCM 1-2116 (ST11)
Group C *Lactobacillus rhamnosus* CGMCC 1.3724 (LPR)

All products were obtained from usual public source. The names "ST11" and "LPR" are abbreviations or nicknames for the cited microorganisms.

Live attenuated measles vaccine (MV-S) purchased from Aventis-Pasteur (Lyon, France).
Measurements
the determination of antibodies to measles virus (IgG1 and IgG2a isotypes) and of total serum IgG was performed by ELISA at the Center for vaccinology and Neonatal Immunology (CVNI) at University Medical center of Geneva (Switzerland), according to standards.
Experimental Procedure:
(FIG. 1 provide a schematic view of the procedure):
1. Four pregnant mice per group received drinking water containing A, B or C throughout pregnancy and during weaning.
2. At weaning (3 weeks) onward, all pups received regular water without any additives. Mothers were sacrificed.
3. At 3 weeks (infant immunization), pups (5-8 pups per litter; 28 pups per group) were immunized with live attenuated measles virus ($5 \times 10^5$ $CCID_{50}$).
4. Pups were monitored weekly (from 3 to 8 weeks of age) for weight gain and feces were collected once a week (from 3 to 8 weeks of age).
5. Pups were bled 3 and 5 weeks after immunization for determination of total IgG and of measles-specific IgG1 and IgG2a antibodies.
6. Five weeks after immunization all mice were sacrificed.
To evaluate differences measles vaccine, Krsukal-Wallis tests followed by Mann-Withney (Wilcoxon) tests were applied.

Results:
FIG. 2 provides a graphic illustration of the results obtained. No effect on the newborn's growth was identified. No differences in vaccine responses related to litters, gender, or specific body weight were observed. A significant increase in antibody responses following measles vaccination was observed in all groups, reflecting a normal antibody maturation process. The immune response was characterized by a mixed Th1:Th2 responses as illustrated by the well-balanced IgG1 and IgG2a levels observed in all groups. Supplementation of mothers with ST11 has no statistically significant effect on pup's responsiveness to measles vaccine (under the testing conditions). However, LPR supplementation to pregnant mothers promoted higher IgG titers compared to controls without altering the general immune profile of the response to measles vaccine.

Conclusion:
These results seem to indicate that the effects are probiotic strain specific. Indeed, ST11 seems to have little effect on pup's intestinal immune maturation and responsiveness to measles vaccine. In contrast, LPR supplementation to pregnant mothers promoted increased peripheral IgG responses to measles vaccine in young adult mice.

Example 2

Mice Study 2
Material and Methods:
Conventional six-week-old pregnant female BALB/c mice (18-20 g) were used in all experiments, purchased from Janvier, France. The mice were housed under specific pathogen free conditions at the Nestle research Center animal facility, and 10 to 12 pups from each litter were allotted to each study group.

Animals had free access to regular conventional diet. Pregnant mice received probiotic or placebo powders suspended in the drinking water. The drinking water was changed every day. Two groups were compared:
Group A control (Maltodextrine)
Group B *Bifidobacterium lactis* CNCM 1-3446 (BL)

All products were obtained from usual public source. The name "BL" is an abbreviation for the cited microorganism.

Tetanus Toxoid vaccine, Tetanol Pur (40 UI) was purchased from Novartis (Switzerland).
Measurements
The determination of spleen T-cell proliferation in presence of anti-CD3 antibody was performed according to standard procedures. Briefly, splenocytes were incubated with plate-bound anti-mouse CD3 (2.5 g/ml incubated 2 h at 37° C., BD Pharmingen, cat no. 553056) in 96-well plates at 37° C. for 72 h. Cell proliferation was determined by the incorporation of [methyl-3H]thymidine (Amersham Pharmacia Biosciences) as described (DeCicco, K. L., Youngdahl, J. D. and Ross, A. C. 2001 Immunology 104, 341-348). Data are represented as counts per minute, normalized by the percentage of CD3-positive cells actually present in the spleen of tested mice.

Dosages of serum IgG antibodies specific to Tetanus Toxoid were performed by ELISA. Briefly, 96-wells microtiter plates were coated with 0.1 μg of whole TT antigen (Calbiochem, Tetanus Toxoid from *Clostridium tetani*, cat no 582231) in PBS. After 3 washings with PBS-0.05% Tween20, plates were blocked with a PBS-20% FCS-0.05% Tween20 buffer for 1 h at 37° C. and then washed 3 times again. Serial dilutions of mice sera in blocking buffer were incubated for 2 h at 37° C. After 3 washings, bound TT-specific IgG were detected by the incubation with a biotin-conjugated goat anti-mouse IgG antibody (Southern-Biotech, cat no. 1034-08) for 1 h at 37° C. Following 3 washings, ELISA plates were incubated with peroxidase labelled streptavidin (KPL, cat no. 14-30-00) for 30 minutes at 37° C. After 3 final washing steps, peroxidase substrate (KPL, cat no. 50-76-00) was added. The colorimetric reaction was blocked with sulfuric acid and optical density at 450 nm was then measured in a spectro-photometer. Antibody titers were then calculated as described (Ma, Y. and Ross, A. C., 2005, Proc Natl Acad Sci. 2005 Sep. 20; 102(38):13556-61).

Experimental Procedure:

(FIG. 3 provide a schematic view of the procedure):

1. Two to three pregnant mice per group received drinking water containing placebo or BL throughout pregnancy and during the first two weeks of lactation.

2. At weaning (3 weeks) onward, all pups received regular water without any additives. Mothers were sacrificed.

3. At 3 weeks a sub-group of pups in each group (5-6 pups per group) was sacrificed to assess the spleen-cell proliferation.

4. At 3 weeks (infant immunization), remaining pups (5-6 pups per group) were immunized sub-cutaneously with TT vaccine (¼ of the human dose).

5. Four weeks after the first immunization a vaccine boost was administered to pups.

6. Pups were bled 4 weeks after the first immunization and 2 weeks after the boost for determination of anti-TT IgG antibodies, then the mice were sacrificed.

To evaluate differences in T-cell proliferation and IT vaccine a Mann-Withney (Wilcoxon) tests were applied.

Results:

FIG. 4 show that a significant increase in antibody responses following TT vaccination was observed in all groups, reflecting a normal antibody maturation process. Supplementation of mums with BL during pregnancy and lactation promoted higher systemic T-cell reactivity and significantly enhanced IgG titers compared to placebo.

Conclusions:

The two studies of examples 1 and 2 highlight the fact that it is possible to promote immune development in offspring through perinatal intervention, in particular via supplementation of mothers during pregnancy and lactation with probiotics. These effects are strain-specific as indicated by the Study 1; however they seem not to be species-specific. Indeed. LPR or BL supplementation to pregnant mothers seems to promote a higher immune maturation in the offspring.

The invention is claimed as follows:

1. A method for improving immunity in an offspring, the method comprising:
   administering to an expecting female mammal daily for all of the gestation period a composition comprising an effective amount of *Lactobacillus rhamnosus* CGMCC 1.3724 so as to boost the immunity of the offspring after birth.

2. The method of claim 1 wherein the administering of the composition to the female mammal induces boosting the innate immune functions and promoting specific immune response to infectious antigens of the offspring.

3. The method of claim 1 wherein the composition reinforces the transmission of immune competences from the female to the offspring.

4. The method of claim 1 wherein the female mammal is human.

5. The method of claim 1 wherein the composition is administered orally to the female.

6. The method of claim 1 wherein the composition is administered to the female mammal for part of the lactation period of the offspring.

7. The method of claim 1 wherein the composition comprises ingredients selected from the group consisting of inulin, fructooligosaccharide (FOS), short-chain fructooligosaccharide (short chain FOS), galacto-oligosaccharide (GOS), xylooligosaccharide (XOS), glanglioside, partially hydrolysed guar gum, acacia gum, soybean-gum, Lacto-wolfberry, wolfberry extracts and mixtures thereof.

8. The method of claim 1 wherein the immunity boost comprises an increase in the ability of the offspring to respond to an antigenic exposure.

9. The method of claim 8 wherein the response to the antigenic exposure comprises an elevation of the specific antibodies to the antigens in the serum, saliva or feces of the offspring.

10. The method of claim 8 wherein the response to the antigenic exposure comprises an elevation of the total polyreactive antibodies in the offspring.

11. The method of claim 8 wherein the response to the antigenic exposure comprises an elevation of cellular immune response in the blood of the offspring.

12. The method of claim 8 wherein the antigenic exposure comprises exposure to at least one agent selected from the group consisting of viruses, bacteria, infective parasites infection and mixtures thereof.

13. The method of claim 8 wherein the increased ability to respond to the antigenic exposure contributes to better protect the offspring against infections in early life.

14. The method of claim 1 wherein the immunity boost reaches its maximum during the lactation period, or during juvenile phase of the offspring.

15. The method of claim 1 wherein the composition is further administered to the offspring during a period selected from the group consisting of lactation, after a full weaning and after a partial weaning.

16. The method of claim 1 wherein the composition is administered in a form selected from the group consisting of food, drinks, dietary supplements and pharmaceutical compositions.

17. The method of claim 1 wherein the immunity boost reaches its maximum between birth (day 0) and day 180 of life.

18. A method for boosting the immunity of an offspring, the method comprising:
   administering to an expecting female mammal daily for all of the gestation period a composition comprising *Lactobacillus rhamnosus* CGMCC 1.3724 in an amount equivalent to between $10^3$ and $10^{10}$ cfu per gram of dry composition so as to boost the immunity of the offspring after birth.

* * * * *